(12) United States Patent
Jeong et al.

(10) Patent No.: US 9,532,765 B2
(45) Date of Patent: Jan. 3, 2017

(54) ULTRASOUND SCANNING ASSISTANCE APPARATUS FOR BREAST CANCER DIAGNOSIS AND METHOD OF ULTRASOUND SCANNING

(71) Applicant: Electronics and Telecommunications Research Institute, Daejeon (KR)

(72) Inventors: Ji Wook Jeong, Daejeon (KR); Soo Yeul Lee, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 148 days.

(21) Appl. No.: 14/217,617

(22) Filed: Mar. 18, 2014

(65) Prior Publication Data

US 2015/0005631 A1 Jan. 1, 2015

(30) Foreign Application Priority Data

Jul. 1, 2013 (KR) ........................ 10-2013-0076280

(51) Int. Cl.
*A61B 8/14* (2006.01)
*A61B 8/08* (2006.01)
*A61B 8/00* (2006.01)

(52) U.S. Cl.
CPC ........... *A61B 8/0825* (2013.01); *A61B 8/4281* (2013.01); *A61B 8/485* (2013.01); *A61B 8/4483* (2013.01)

(58) Field of Classification Search
CPC ... A61B 8/0825; A61B 8/4281; A61B 8/4483; A61B 8/485
See application file for complete search history.

(56) References Cited

U.S. PATENT DOCUMENTS

| | | | |
|---|---|---|---|
| 2007/0092059 A1* | 4/2007 | Eberhard | A61B 6/502 378/37 |
| 2010/0179429 A1 | 7/2010 | Ho et al. | |
| 2010/0222667 A1* | 9/2010 | Osman | A61B 5/0555 600/422 |
| 2012/0089026 A1 | 4/2012 | Wang et al. | |
| 2012/0136250 A1 | 5/2012 | Tabaru et al. | |

* cited by examiner

*Primary Examiner* — Mark Remaly
(74) *Attorney, Agent, or Firm* — Kile Park Reed & Houtteman PLLC

(57) ABSTRACT

An ultrasound scanning assistance apparatus for diagnosis of a breast cancer is provided. The ultrasound scanning assistance apparatus includes a fixing container including a scan surface to scan an ultrasound transducer adapted to diagnose a breast cancer and a soft membrane to contact a surface of a human body; and a buffer fluid controller to control a hydraulic pressure of a buffer fluid filling the fixing container.

14 Claims, 5 Drawing Sheets

301  Auxiliary scanning

ULTRASOUND SCANNING ASSISTANCE APPARATUS FOR BREAST CANCER DIAGNOSIS AND METHOD OF ULTRASOUND SCANNING

CROSS-REFERENCE TO RELATED APPLICATION

This application claims the benefit of Korean Patent Application No. 10-2013-0076280, filed on Jul. 1, 2013, in the Korean Intellectual Property Office, the disclosure of which is incorporated herein by reference.

BACKGROUND

1. Field of the Invention

The present invention relates to an ultrasound scanning assistance apparatus for diagnosis of a breast cancer and an ultrasound scanning method, and more particularly, to an ultrasound scanning assistance apparatus that hermetically contacts a skin of a human body part using a dedicated soft membrane and ultrasonically images the human body part being contacted.

The present invention is derived from a research conducted as part of the new technology convergence type growth engine program with the support of the Korea science and engineering foundation funded by the ministry of education and science technology. [Grant number: 2012K001520, Title: Development in a lesion detection technology for a breast ultrasound.]

2. Description of the Related Art

Globally, a breast cancer takes the first ranking of incidence of female cancers. In Korea, most of breast cancer patients are young at the age of forties. Mammography is generally used in diagnosis of the breast cancer. However, in regard to oriental women with over 40% of dense breast tissue, efficiency of the mammography is relatively low, that is, no more than 0.6% of a positive predictive value. Therefore, two-dimensional (2D) breast ultrasound imaging has been additionally performed. In this case, a breast cancer detection rate reaches about 95% or more. A three-dimensional (3D) breast ultrasound, which is being recently developed, easily identifies a location, size, and shape of a tumor, increases diagnosis accuracy of the breast cancer, and facilitates biopsies for a definitive diagnosis and treatment.

When performing the 3D breast ultrasound imaging, a meaningful image may be obtained only when a transducer device scans a skin in close contact with the skin so that the ultrasound effectively propagates through a human body. For this, gel-type assistant fluid needs to be disposed between the transducer device and the skin without air intervened.

A generally used method for the 3D ultrasound imaging outputs an ultrasonic signal from a transducer device such as a one-dimensional (1D) array lead zirconate titanate (PZT), and analyzes and post-processes a time interval between reflected signals, thereby reproducing a 2D image. In addition, the method constructs information with respect to a 3D space by continuously obtaining a 2D image slice by moving a transducer array in a direction orthogonal to the 1D array. According to a recently researched method, a 3D image may be simultaneously reproduced directly from a transducer device having a 2D array.

The 1D transducer method needs scanning of a transducer and therefore has a limit in synchronism. That is, a difference in obtaining time of an image between start and end of scanning need to be taken into consideration in reading. When a plurality of 3D images are obtained by a plurality of transducers and integrated into an entire 3D image, a mismatch between images obtained by the plurality of transducers may be generated. Furthermore, since the images are obtained on a time basis, a movement of a human body during the image obtainment needs to be considered. (Refer to US 2010/0179429 A1 FIGS. 1 and 6b, and US 2012/0089026 A1 FIG. 4a)

Recently, elastography showing an exclusive performance in tumor diagnosis is being spotlighted as a functional ultrasound imaging method. Elastography reconstructs an elastic property image using a difference between ultrasound images obtained by oscillating a particular surface of a human body at a short time interval of about tens of hertz (Hz) from an outside, and visualizes a change in human parenchymal properties, in particular, elastic properties. In case of diagnosis of a breast cancer, the elastography is particularly useful in determining malignancy and benignancy of a tumor since the elastic properties are obviously different between a malignant tumor, which is several times harder than a surrounding parenchyma, and the surrounding parenchyma in an image obtained by the elastography.

However, since the elastography extracts the elastic properties by applying oscillation to the human body at a short time interval, a method of applying oscillation directly influences an image quality. In addition, a structural problem may be caused since an ultrasound needs to be generated and collected by a transducer simultaneously with when a change in the elastic properties of the human body occurs. That is, in a conventional system, an oscillation apparatus of tens of Hz is operated integrally with a portable transducer and, at this time, an ultrasound image is simultaneously obtained using the transducer. In this case, a difference image is obtained by oscillating only a portion contacting the transducer. However, since oscillation is also generated from the portable transducer, it is difficult to maintain constant oscillation. (Refer to 2012/0136250 A1 FIG. 2)

SUMMARY

An aspect of the present invention provides an ultrasound scanning assistance apparatus and an ultrasound scanning method providing an ultrasound imaging apparatus for achieving synchronism when a plurality of three-dimensional (3D) images are scanned and integrated and a method of performing elastography, the ultrasound scanning assistance apparatus and the ultrasound scanning method also performing conventional 3D ultrasound imaging and elastography for diagnosis of a breast cancer.

Another aspect of the present invention provides an ultrasound scanning assistance apparatus providing increased resolution and imaging speed in diagnosis of a breast cancer, and providing both an ultrasound image and an elastography image without adding a dedicated structure, thereby increasing accuracy in identifying malignancy and benignancy of a tumor, and an ultrasound scanning method.

According to an aspect of the present invention, there is provided an ultrasound scanning assistance apparatus including a fixing container including a scan surface to scan an ultrasound transducer adapted to diagnose a breast cancer and a soft membrane to contact a surface of a human body; and a buffer fluid controller to control a hydraulic pressure of a buffer fluid filling the fixing container.

According to another aspect of the present invention, there is provided an ultrasound scanning method including bringing a soft membrane that hermetically applies or releases pressure on a surface of a human body, into contact with the surface of the human body; controlling a hydraulic pressure of a buffer fluid filling a fixing container which includes the soft membrane as a surface and an ultrasound transducer for diagnosing a breast cancer as a scan surface; and obtaining an ultrasound image by scanning the human body according to at least one of an ultrasound imaging method and an elastography method for diagnosing the breast cancer.

EFFECT

According to embodiments of the present invention, an ultrasound scanning assistance apparatus and an ultrasound scanning method may provide an ultrasound imaging apparatus for achieving synchronism when a plurality of three-dimensional (3D) images are scanned and integrated and a method of performing elastography, while performing conventional 3D ultrasound imaging and elastography for diagnosis of a breast cancer.

Additionally, according to embodiments of the present invention, an ultrasound scanning assistance apparatus and an ultrasound scanning method provide increased resolution and imaging speed in diagnosis of a breast cancer, and provide both an ultrasound image and an elastography image without adding a dedicated structure, thereby increasing accuracy in identifying malignancy and benignancy of a tumor.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Reference will now be made in detail to exemplary embodiments of the present invention, examples of which are illustrated in the accompanying drawings, wherein like reference numerals refer to the like elements throughout.

Figure 1:
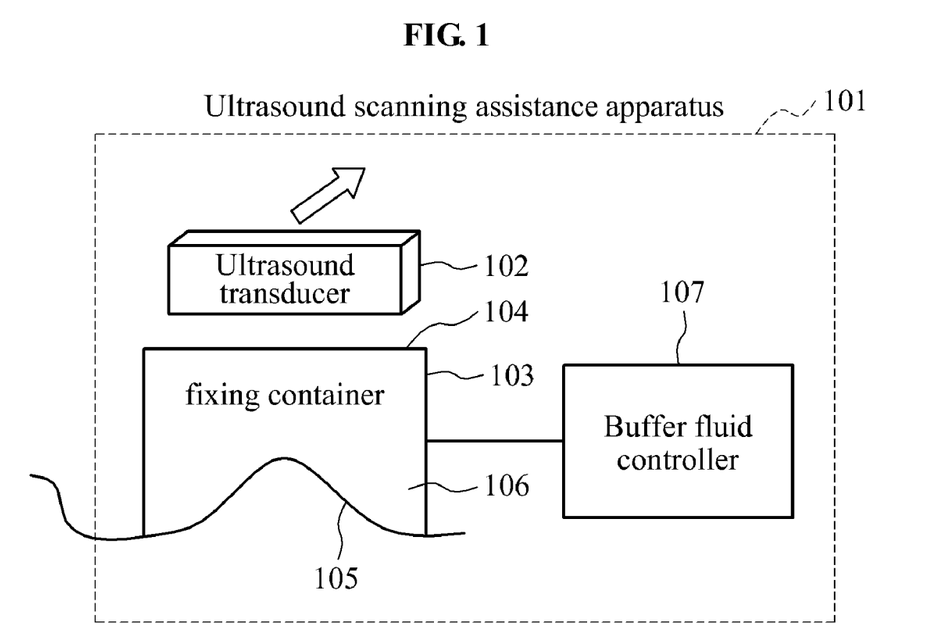
FIG. 1 is a diagram illustrating an ultrasound scanning assistance apparatus according to an embodiment of the present invention.

FIG. 1 is a diagram illustrating an ultrasound scanning assistance apparatus 101 according to an embodiment of the present invention.

Referring to FIG. 1, the ultrasound scanning assistance apparatus 101 may be used to obtain a three-dimensional (3D) image of an inside of a human body to diagnose a breast cancer. The ultrasound scanning assistance apparatus 101 may hermetically contacts a partial skin of the human body using a dedicated soft membrane 105, thereby obtaining the 3D image of the inside of the human body. The obtained 3D image may be used for various purposes such as diagnosis of a breast cancer. During ultrasound imaging, a user may apply a buffer fluid 106 to a surface of the human body for contact with the soft membrane 105. When the buffer fluid 106 is applied to the human body, contact efficiency with respect to the soft membrane 105 may be increased and an ultrasound may pass through the human body with a minimum reflectance.

The ultrasound scanning assistance apparatus 101 may include an ultrasound transducer 102, a fixing container 103, and a buffer fluid controller 107.

The ultrasound transducer 102 may generate an ultrasound for diagnosing the breast cancer, and collect images of the ultrasound passed through a human body according to the generated ultrasound. When obtaining an elastography image, the ultrasound transducer 102 may obtain the elastography image corresponding to a shift image based on the obtained ultrasound image, primarily, and by calculating a change in the ultrasound image according to a unit shift of the obtained ultrasound image. A process of obtaining the elastography image will be described specifically with reference to FIG. 4.

The fixing container 103 may include a scan surface 104 for scanning the ultrasound transducer 102 and the soft membrane 105 for contacting a surface of a human body. Here, the scan surface 104 and the soft membrane 105 may be different surfaces. The fixing container 103 may include the buffer fluid 106 of which a hydraulic pressure is controlled to apply or release pressure on the surface of the human body during ultrasound imaging. The scan surface 104 may be adapted to guide the ultrasound transducer 102 so that the ultrasound transducer 102 may obtain the 3D ultrasound image of the inside of the human body.

The buffer fluid controller 107 may oscillate the human body at uniform intervals by controlling injection of the buffer fluid 106 by generating a change in the human body. That is, when taking the elastography image in synchronization with the fixing container 103 of the ultrasound transducer 102, the buffer fluid controller 107 may control a hydraulic pressure of the buffer fluid 106 or injection of the buffer fluid 106 so that the elastography image with respect to a part of the human body may be taken.

The buffer fluid 106, the soft membrane 105, and the fixing container 103 included in the ultrasound scanning assistance apparatus 101 may be made of a material that minimizes reflectance when the ultrasound is transmitted.

Figure 2:
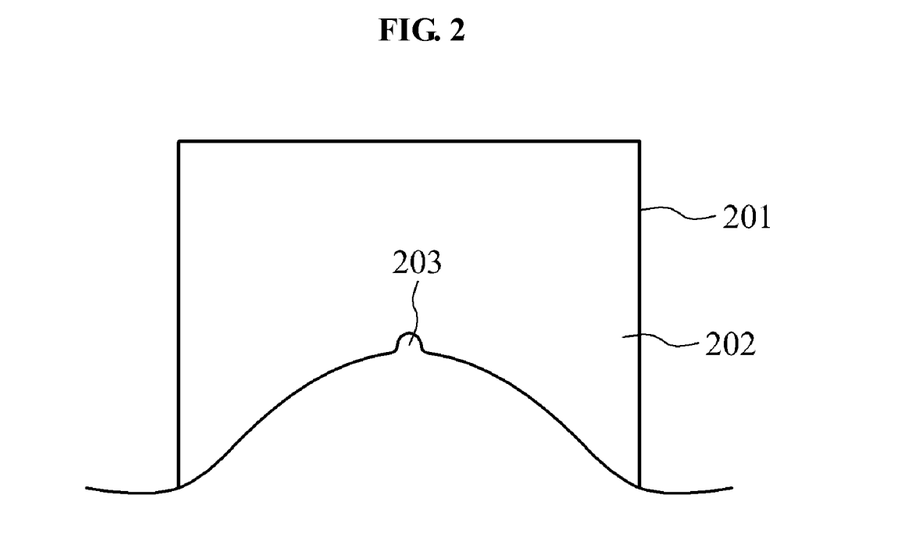
FIG. 2 is a diagram illustrating formation of a soft membrane according to a protruding portion of a human body, according to an embodiment of the present invention.

FIG. 2 is a diagram illustrating formation of a soft membrane 201 according to a protruding portion 203 of a human body, according to an embodiment of the present invention.

Referring to FIG. 2, the soft membrane 201 refers to a part of a soft membrane, the part of which a surface curvature is optimized corresponding to a body surface of a user. That is, the surface curvature is optimized in advance to suit to characteristics of the user. Therefore, the soft membrane 201 may be custom-made according to a body model of the user. When the soft membrane 201 is custom-made according to the body of the user, buffering and airtightness with respect to the body of the user may be more secured. In addition, oscillation of the soft membrane according to hydraulic oscillation of a buffer fluid 202 which is periodically generated may be transmitted to the human body more uniformly.

The soft membrane 201 may include a general type soft membrane. The general type soft membrane refers to a soft membrane applicable to bodies of various users rather than being custom-made for the body of the user.

The soft membrane of the soft membrane 201 may be formed in consideration of the protruding portion 203 of the body surface of the user. For example, the soft membrane may include a portion formed corresponding to the protruding portion 203, for example a nipple, of the body surface of the user. When the soft membrane 201 of the soft membrane is formed in consideration of the protruding portion 203, a mismatch between ultrasound images according to a temporal change during tracking and management of a breast cancer, or an error factor in change analysis such as tracking and management of tumor characteristics may be minimized.

To maximize airtightness with respect to the human body, the soft membrane 201 may be added with or replaced by a rubber material such as caulking or equivalent functional part.

Figure 3A:
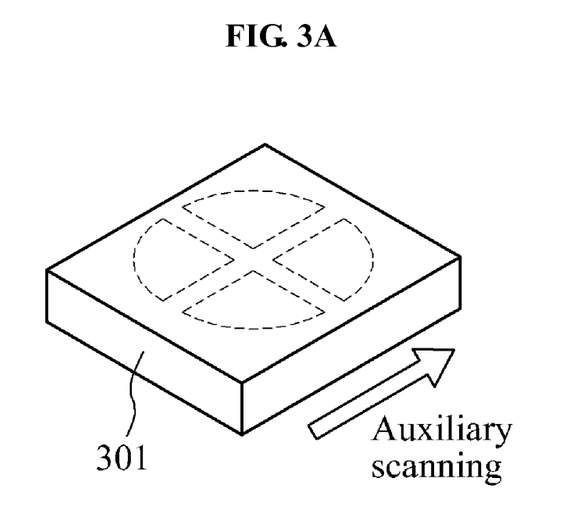
FIGS. 3A and 3B are diagrams illustrating a process of scanning a human body with reference to the protruding portion of the human body, according to an embodiment of the present invention.
Figure 3B:
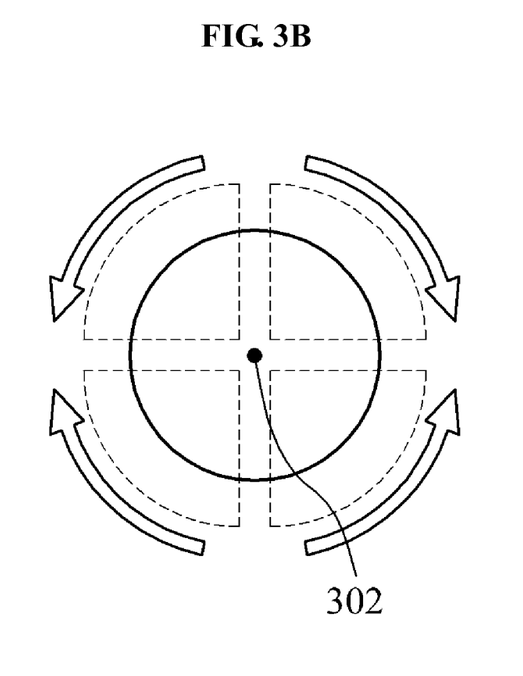

FIGS. 3A and 3B are diagrams illustrating a process of scanning a human body with reference to a protruding portion 302 of the human body, according to an embodiment of the present invention.

Referring to FIGS. 3A and 3B, a scan surface constituting a fixing container refers to a surface that guides an ultrasound transducer 301. In consideration of the surface of the human body, the scan surface may include at least one of a polyhedron, a slope of a cone, and an elliptical curved surface although not limited the foregoing examples. When the scan surface is the elliptical curved surface, the scan surface may have an equal curvature in a circumferential direction with reference to the protruding portion 302 of a surface a body part of the user. The ultrasound transducer 301 may scan the body part, moving on the curved surface in the circumferential direction.

When the scan surface is used as the elliptical curved surface, the ultrasound transducer 301 may perform scanning by dividing a plane of the scan surface into 2n scan areas. With respect to n-pairs of the ultrasound transducers 301 having neighboring scan areas, an ultrasound image obtained at start of scanning or an ultrasound image obtained at end of scanning accords to an ultrasound image of a neighboring ultrasound transducer 301 at a same spot or same time point. Therefore, the ultrasound transducers 301 may secure a scan image advantageous in matching for an integrated image with respect to the ultrasound image.

In addition, since the ultrasound transducer 301 obtains the ultrasound image of the inside of the human body by moving in an arrowed direction on a hard surface according to the scan surface, image distortion where a human body surface is deformed in a back and forth direction may be minimized. The ultrasound transducer 301 may scan an image of a lateral side of the human body using an auxiliary transducer as shown in a lateral side of the ultrasound transducer 301 of FIG. 3A. Therefore, the ultrasound transducer 301 may be used in compensation of an image distortion and the like.

Figure 4:
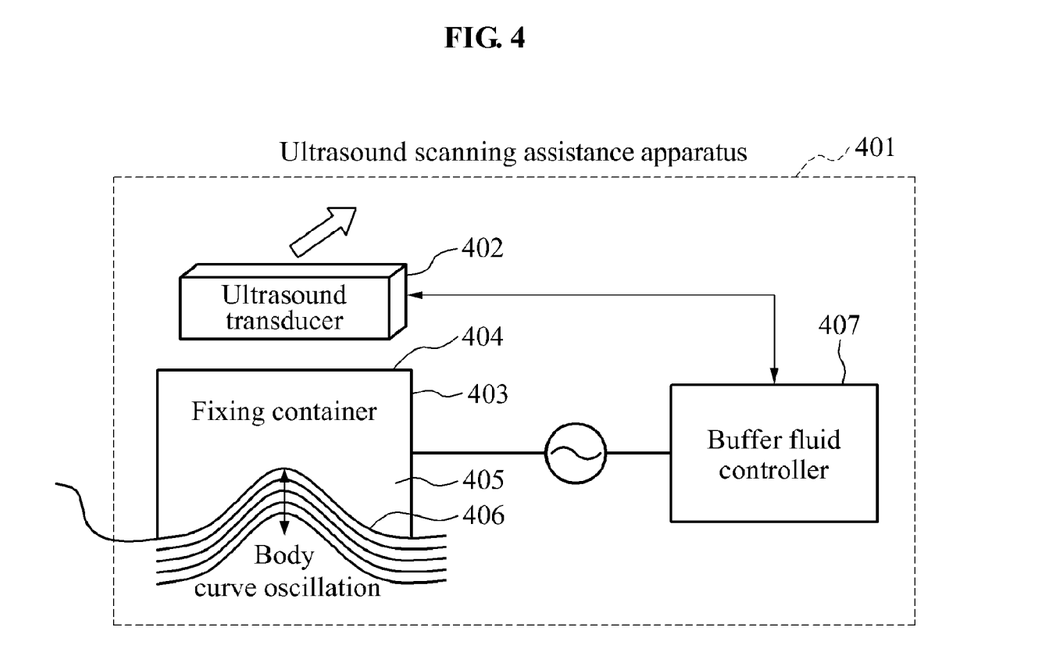
FIG. 4 is a diagram illustrating an ultrasound scanning assistance apparatus used for elastography, according to an embodiment of the present invention.

FIG. 4 is a diagram illustrating an ultrasound scanning assistance apparatus 401 used for elastography, according to an embodiment of the present invention.

Referring to FIG. 4, the ultrasound scanning assistance apparatus 401 may be used for taking an elastography image and, for this purpose, may scan a human body using a buffer fluid controller 407 synchronized with a fixing container 403 or a scan surface 404 for guiding an ultrasound transducer 402.

In detail, when taking the elastography image, the ultrasound scanning assistance apparatus 401 may generate a hydraulic change at time intervals of tens of Hz to generate an actual shift to the human body. Here, the ultrasound scanning assistance apparatus 401 may periodically generate the hydraulic change using the buffer fluid controller 407. As a buffer fluid 405 filling the fixing container 403 is controlled by the buffer fluid controller 407, a soft membrane 406 may apply or release pressure on the surface of the human body contacting the fluid human body corresponding to the hydraulic change. As the surface of the human body is pressed or released, a shift may be uniformly generated throughout the surface of the human body.

The ultrasound scanning assistance apparatus 401 may obtain a primary ultrasound image by moving over the surface of the human body, using the synchronized ultrasound transducer 402. The ultrasound scanning assistance apparatus 401 may calculate a change in the ultrasound image according to a unit shift based on the obtained ultrasound image, and may obtain an elastography image by deriving a shift image. In detail, the ultrasound scanning assistance apparatus 401 may obtain an n-th degree shift component of the ultrasound image to be derived, using an n-th degree difference formula, from data related to a plurality of ultrasound images obtained by controlling a shift generation amount and intervals. The ultrasound scanning assistance apparatus 401 may facilitate analysis of body parts having different elastic properties, by comparing functional ultrasound images obtained through the foregoing method. Here, the functional ultrasound images may refer to the elastography images. Comparison of the functional ultrasound images may refer to comparison of ultrasound images taken at different times and, on different dates, with/without contrast agents, and with/without Doppler sonography corresponding to a currently obtained ultrasound image.

Diagnosis and treatment of a breast cancer are performed based on obtainment of an accurate ultrasound image. Therefore, tracking and management of the breast cancer is significant in diagnosis of the breast cancer. Therefore, comparison between ultrasound images is necessary in diagnosing the breast cancer. However, comparison between ultrasound images taken on different dates and at different times may cause a mismatch between the ultrasound images. The ultrasound scanning assistance apparatus 401 may form a soft membrane including a nipple-shape protruding structure according to a body surface of a user to minimize the mismatch between the ultrasound images. Accordingly, the ultrasound scanning assistance apparatus 401 may obtain an ultrasound image more advantageous for matching of the ultrasound images. In addition, the advantageous ultrasound image may be an image having a higher matching efficiency than an ultrasound image obtained by reimaging for tracking a change in a lesion of the user.

Also, the advantageous ultrasound image may be an image obtained under a same condition in consideration of information on a particular direction of body parts of the user, for example a neck and shoulders, with reference to the protruding portion, to increase accuracy of matching.

Therefore, the ultrasound scanning assistance apparatus 401 may facilitate analysis between the body parts for diagnosis of the breast cancer, by comparing the functional ultrasound images having a relatively high matching efficiency between ultrasound images.

In addition, the ultrasound scanning assistance apparatus 401 may obtain the ultrasound image in consideration of a position of the user when taking the ultrasound image. For example, the ultrasound scanning assistance apparatus 401 may obtain the ultrasound image of a human body in a stable position, by adding a dedicated tool such as a belt or a marker for correction of various positions such as sitting, lying on a face, lying on a back, and lying on a side.

The ultrasound scanning assistance apparatus 401 may take the ultrasound image with a same hydraulic pressure when performing reimaging, based on a hydraulic pressure used during initial imaging of a user. The initial hydraulic pressure may be used as a parameter for maintaining a surface state of a same user.

Figure 5:
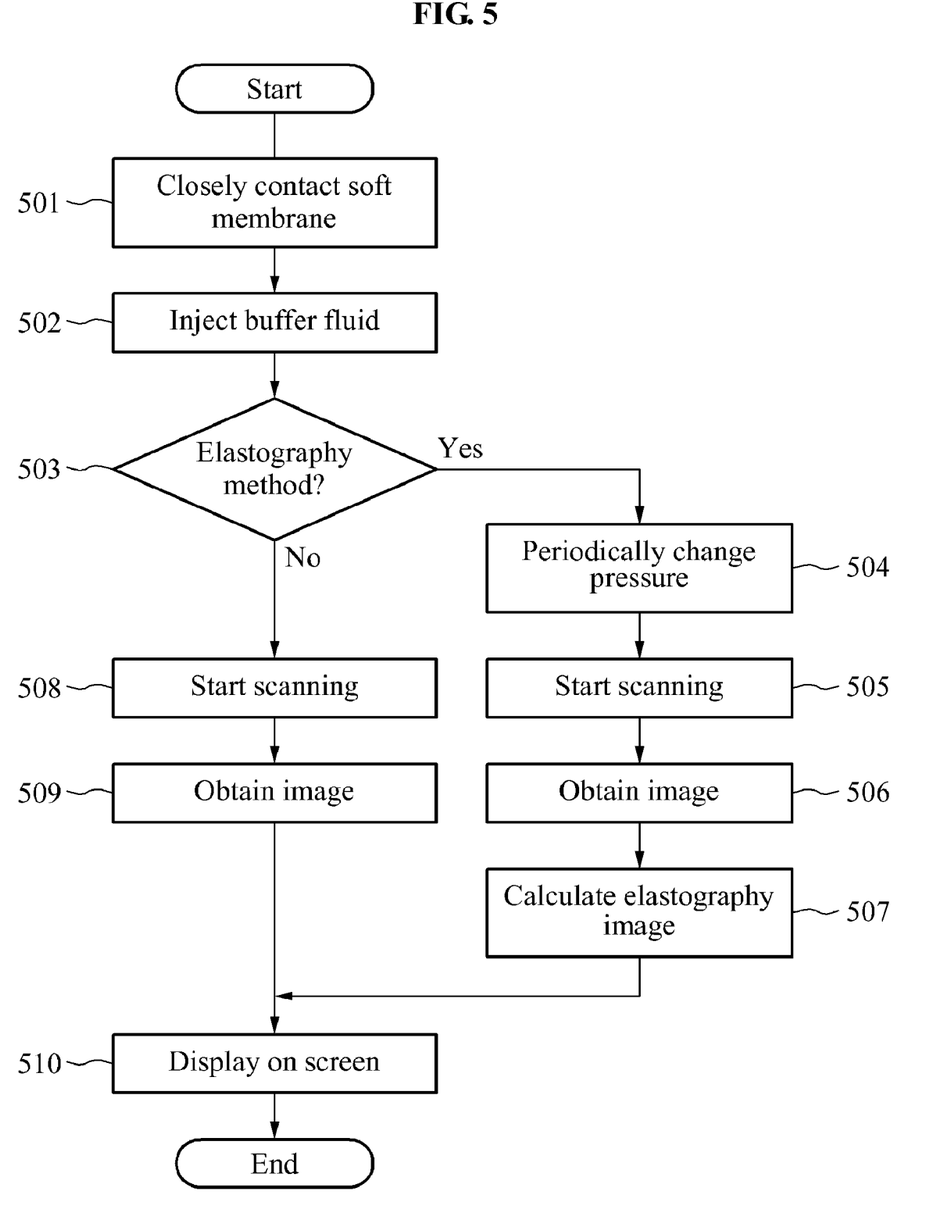
FIG. 5 is a block diagram illustrating of an ultrasound scanning process according to an embodiment of the present invention.

FIG. 5 is a block diagram illustrating of an ultrasound scanning process according to an embodiment of the present invention.

In operation 501, an ultrasound scanning assistance apparatus may bring a soft membrane constituting a fixing container into close contact with a surface of a human body, corresponding to a position of a user. The user may be a patient who wants diagnosis of a breast cancer. A dedicated buffer fluid may be applied to a body part to be imaged, to minimize reflectance during ultrasound transmission based on ultrasound transmission characteristics. The buffer fluid applied to the surface of the human body may maximize the close contact. A soft membrane may include a custom-made type dedicatedly made for a body of the user and a general type applicable to all users. Although not shown, the ultrasound scanning assistance apparatus may further include a hydraulic pressure controller for hermetic contact between the human body and the soft membrane.

In operation 502, the ultrasound scanning assistance apparatus may inject a buffer fluid filling the fixing container using a buffer fluid controller in consideration of a hydraulic pressure measured right before ultrasound imaging to obtain an ultrasound image or a hydraulic pressure measured to reproduce a diseased part maintained at the time of previous imaging.

In operation 503, the ultrasound scanning assistance apparatus may check whether a current imaging method is the elastography method. Here, when the ultrasound image is taken by the elastography method, the ultrasound scanning assistance apparatus may perform operation 504. When the imaging method is not the elastography method but the ultrasound imaging method, the ultrasound scanning assistance apparatus may perform operation 508.

In operation 504 in which the elastography method is used, the ultrasound scanning assistance apparatus may control a hydraulic pressure of the buffer fluid at uniform intervals through the buffer fluid controller to generate a change in the human body. Here, since the ultrasound scanning assistance apparatus periodically changes a hydraulic pressure, the change may be uniformly generated throughout the surface of the human body. The ultrasound scanning assistance apparatus may change the hydraulic pressure based on a repetition period and a hydraulic shift dedicatedly set with reference to the hydraulic pressure of the buffer fluid injected in operation 502.

In operation 505, the ultrasound scanning assistance apparatus may start scanning for obtaining an ultrasound image of an inside of the human body. In operation 506, the ultrasound scanning assistance apparatus may obtain the ultrasound image of the inside of the human body being in close contact with the soft membrane. In detail, the ultrasound scanning assistance apparatus may obtain the ultrasound image by operating an ultrasound transducer in synchronization with pulses of the changing hydraulic pressure.

In operation 507, the ultrasound scanning assistance apparatus may calculate zeroth, first, . . . , (n−1)th degree shift images from an n-number of obtained ultrasound images. For example, the ultrasound scanning assistance apparatus may obtain an (n−1)th gradient magnitude image, an (n−1)th shear stress image, and the like using an (n−1)th degree difference formula for calculation of an elastography image according to elastic properties.

In operation 508 in which the ultrasound imaging method is used, the ultrasound scanning assistance apparatus may start scanning for obtaining the ultrasound image of the inside of the human body. In operation 509, the ultrasound scanning assistance apparatus may obtain the ultrasound image by operating at least one ultrasound transducer while maintaining the hydraulic pressure of the buffer fluid injected in operation 502.

In operation 510, the ultrasound scanning assistance apparatus may display at least one of the ultrasound image obtained in operation 507 and the ultrasound image obtained in operation 509.

When displaying the ultrasound image obtained in operation 507, the ultrasound scanning assistance apparatus may overlay the shift image or a particular interested area of an image of the elastic properties on a simultaneously taken ultrasound image. In this case, moreover, the ultrasound scanning assistance apparatus may separately display a portion having obviously different elastic properties from a surrounding parenchyma.

Figure 6:
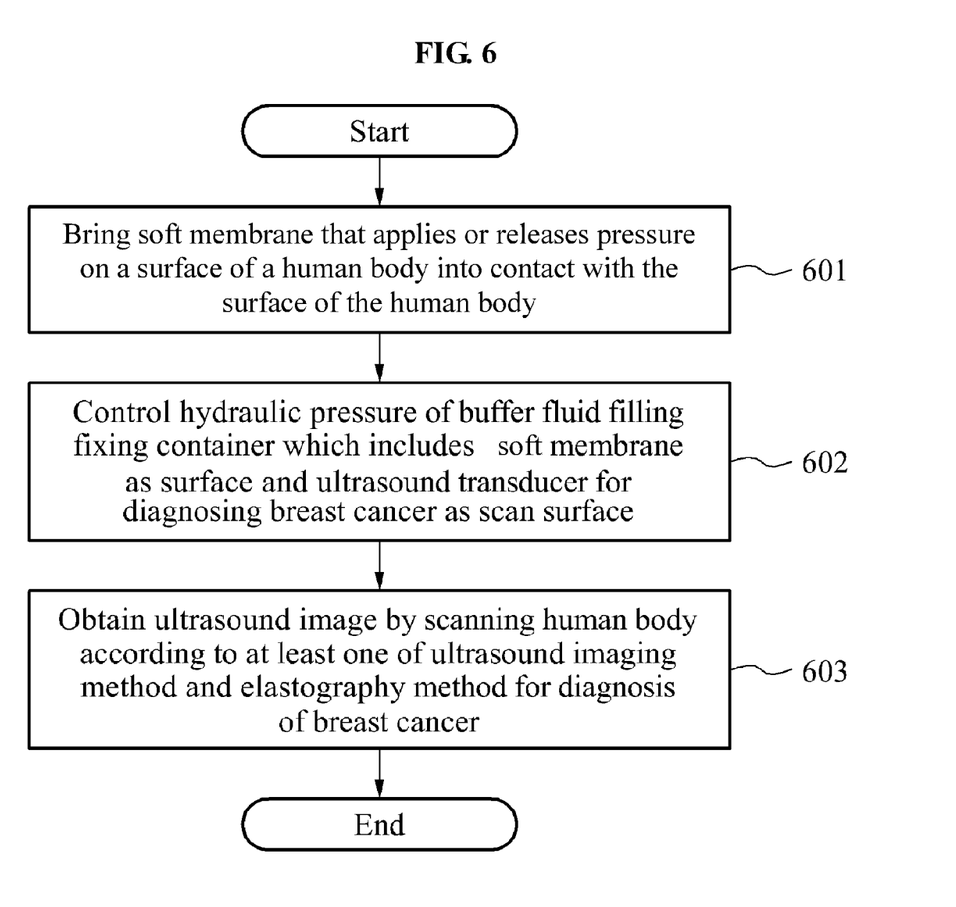
FIG. 6 is a flowchart illustrating an ultrasound scanning method according to an embodiment of the present invention.

FIG. 6 is a flowchart illustrating an ultrasound scanning method according to an embodiment of the present invention.

In operation 601, an ultrasound scanning assistance apparatus may bring a soft membrane, which hermetically applies or releases pressure on a surface of a human body, into contact with the surface of the human body. The soft membrane may be optimized to a curvature of the surface of the human body corresponding to characteristics of a user. The soft membrane may be custom-made according to a body model of the user and, in this case, more secure buffering and airtightness with respect to the body of the user may be achieved. Furthermore, oscillation of a soft human body according to periodic hydraulic oscillation of the buffer fluid may be transmitted to the human body more uniformly.

In operation 602, the ultrasound scanning assistance apparatus may control a hydraulic pressure of the buffer fluid filling a fixing container which includes the soft membrane as a surface and an ultrasound transducer for diagnosing a breast cancer as a scan surface. The ultrasound scanning assistance apparatus may apply or release pressure on the surface of the human body being in close contact with the soft membrane, by controlling the hydraulic pressure of the buffer fluid.

In operation 603, the ultrasound scanning assistance apparatus may obtain the ultrasound image by scanning the body of the user according to at least one of the ultrasound imaging method and the elastography method for diagnosing the breast cancer. When the ultrasound imaging method is used, the ultrasound scanning assistance apparatus may obtain the ultrasound image by performing scanning with single or plural ultrasound transducers while maintaining the hydraulic pressure controlled in the operation of controlling the hydraulic pressure of the buffer fluid. When the elastography method is used, the ultrasound scanning assistance apparatus may change the hydraulic pressure based on a repetition period and a hydraulic shift dedicatedly set using a buffer fluid controller that controls the hydraulic pressure with reference to the hydraulic pressure controlled in the operation of controlling the hydraulic pressure of the buffer fluid. In addition, the ultrasound scanning assistance apparatus may obtain the ultrasound image by operating the ultrasound transducer in synchronization with pulses of the changed hydraulic pressure, and may extract a shift image from the obtained ultrasound image.

In addition, the ultrasound scanning assistance apparatus may obtain the ultrasound image according to the elastography image through calculation of an image of the elastic properties from the extracted shift image.

The above-described embodiments of the present invention may be recorded in non-transitory computer-readable media including program instructions to implement various operations embodied by a computer. The media may also include, alone or in combination with the program instructions, data files, data structures, and the like. The program instructions recorded on the media may be those specially designed and constructed for the purposes of the embodiments, or they may be of the kind well-known and available to those having skill in the computer software arts.

Although a few exemplary embodiments of the present invention have been shown and described, the present invention is not limited to the described exemplary embodiments. Instead, it would be appreciated by those skilled in the art that changes may be made to these exemplary embodiments without departing from the principles and spirit of the invention, the scope of which is defined by the claims and their equivalents.

What is claimed is:

1. An ultrasound scanning apparatus comprising:
   an ultrasound transducer that generates an ultrasound;
   a fixing container including a scan surface that guides the ultrasound transducer adapted to diagnose a breast cancer and a soft membrane to contact a surface of a human body; and
   a buffer fluid controller that controls a hydraulic pressure of a buffer fluid filling the fixing container to apply and release pressure on the soft membrane,
   wherein the ultrasound scanning apparatus obtains an ultrasound image by scanning the human body according to at least one of an ultrasound imaging method and an elastography method for diagnosing the breast cancer.

2. The ultrasound scanning apparatus of claim 1, wherein a surface curvature of the soft membrane of the fixing container corresponds to a body surface of a user.

3. The ultrasound scanning apparatus of claim 1, wherein the soft membrane of the fixing container includes a portion that corresponds to a protruding portion included in the surface of the human body.

4. The ultrasound scanning apparatus of claim 1, wherein the soft membrane is made of rubber.

5. The ultrasound scanning apparatus of claim 1, wherein the soft membrane hermetically contacts the surface of the human body according to control of the hydraulic pressure of the buffer fluid by the buffer fluid controller.

6. The ultrasound scanning apparatus of claim 1, wherein the scan surface comprises at least one of a polyhedron, a slope of a cone, and an elliptical curved surface.

7. The ultrasound scanning apparatus of claim 3, wherein the scan surface has an equal curvature in a circumferential direction with reference to the protruding portion.

8. The ultrasound scanning apparatus of claim 3, wherein the ultrasound transducer collects images of the ultrasound passed through the human body by hermetically contacting the surface of the human body using the soft membrane, while moving over a curved surface of the surface of the human body to be scanned in a circumferential direction with reference to the protruding portion.

9. The ultrasound scanning apparatus of claim 1, wherein the buffer fluid controller oscillates the human body at uniform time intervals by controlling injection of the buffer fluid to generate a change in the human body.

10. The ultrasound scanning apparatus of claim 1, wherein the ultrasound transducer obtains the ultrasound image according to the surface of the human body, calculates a change in the ultrasound image according to a unit shift of the obtained ultrasound image, and obtains an elastography image corresponding to a shift image.

11. The ultrasound scanning apparatus of claim 1, wherein the ultrasound imaging method obtains the ultrasound image by performing scanning with single or plural ultrasound transducers while maintaining the hydraulic pressure controlled during the controlling of the hydraulic pressure of the buffer fluid.

12. The ultrasound scanning apparatus of claim 1, wherein the controlled hydraulic pressure is a hydraulic pressure measured by the buffer fluid controller right before ultrasound imaging for obtaining the ultrasound image or a hydraulic pressure measured by the buffer fluid controller to reproduce a diseased part maintained at the time of previous imaging.

13. The ultrasound scanning apparatus of claim 1, wherein the elastography method changes the hydraulic pressure according to a repetition period and a hydraulic shift dedicatedly set using a buffer fluid controller that controls the hydraulic pressure with reference to the hydraulic pressure controlled during the controlling of the hydraulic pressure of the buffer fluid.

14. The ultrasound scanning apparatus of claim 13, wherein the elastography method obtains the ultrasound image by operating the ultrasound transducer in synchronization with pulses of the changed hydraulic pressure, and extracts a shift image from the obtained ultrasound image.

* * * * *